(12) United States Patent
Agus et al.

(10) Patent No.: US 12,085,568 B2
(45) Date of Patent: Sep. 10, 2024

(54) MACHINE LEARNING FOR DIGITAL PATHOLOGY

(71) Applicant: University of Southern California, Los Angeles, CA (US)

(72) Inventors: David B. Agus, Beverly Hills, CA (US); Paul Thomas Macklin, Bloomington, IN (US); Rishi Raghav Rawat, Boulder, CO (US); Daniel Lee Ruderman, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 18/387,608

(22) Filed: Nov. 7, 2023

(65) Prior Publication Data

US 2024/0069026 A1  Feb. 29, 2024

Related U.S. Application Data

(63) Continuation of application No. 16/491,700, filed as application No. PCT/US2018/021060 on Mar. 6, 2018, now Pat. No. 11,835,524.
(Continued)

(51) Int. Cl.
*G06K 9/00* (2022.01)
*G01N 33/574* (2006.01)
(Continued)

(52) U.S. Cl.
CPC ......... *G01N 33/574* (2013.01); *G06F 18/211* (2023.01); *G06T 7/0012* (2013.01);
(Continued)

(58) Field of Classification Search
None
See application file for complete search history.

(56) References Cited

U.S. PATENT DOCUMENTS

2014/0101080 A1   4/2014 Lee et al.
2015/0376712 A1  12/2015 Ray et al.
(Continued)

FOREIGN PATENT DOCUMENTS

WO   2005/001740 A2   1/2005
WO   2010/024926 A2   3/2010
(Continued)

OTHER PUBLICATIONS

Bychkov, D. et al., "Deep learning based tissue analysis predicts outcome in colorectal cancer," Scientific Reports, (2018), pp. 1-11 (found at www.nature.com/articles/s41598-018-21758-3).
(Continued)

*Primary Examiner* — Wei Wen Yang
(74) *Attorney, Agent, or Firm* — Brooks Kushman P.C.

(57) ABSTRACT

A method assessing tissue morphology using machine learning includes a step of training a machine learnable device to predict the status of a diagnostic feature in stained tissue samples. The machine learnable device is trained with a characterized set of digital images of stained tissue samples. Each digital image of the characterized set has a known status for the diagnostic feature and an extracted feature map provides values for a extracted feature over an associated 2-dimensional grid of spatial locations. A step of inputting the set of extracted feature maps is inputted into the machine learnable device to form associations therein between the set of extracted feature maps to and the known status for the diagnostic feature to form a trained machine learnable device. The status for the diagnostic feature of a stained tissue sample of unknown status for the diagnostic feature is predicted from the trained machine learnable device.

22 Claims, 11 Drawing Sheets

Related U.S. Application Data

Figure 1:
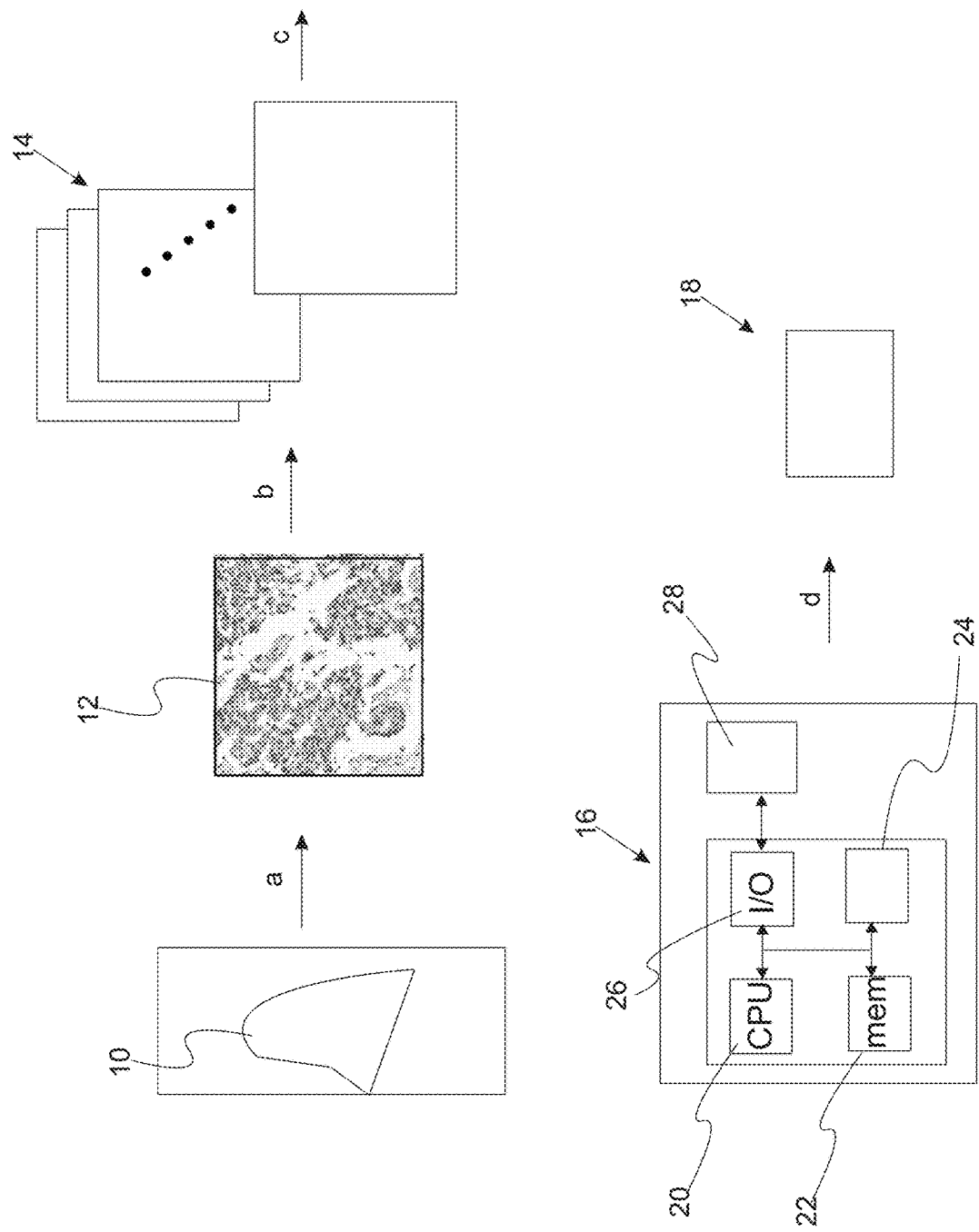

(60) Provisional application No. 62/467,579, filed on Mar. 6, 2017.

(51) Int. Cl.
| | |
|---|---|
| *G06F 18/211* | (2023.01) |
| *G06T 7/00* | (2017.01) |
| *G06V 10/82* | (2022.01) |
| *G06V 20/69* | (2022.01) |
| *G16H 50/20* | (2018.01) |

(52) U.S. Cl.
CPC ............ *G06V 10/82* (2022.01); *G06V 20/695* (2022.01); *G06V 20/698* (2022.01); *G16H 50/20* (2018.01); *G06T 2207/10024* (2013.01); *G06T 2207/20081* (2013.01); *G06T 2207/20084* (2013.01); *G06T 2207/30024* (2013.01)

(56) References Cited

U.S. PATENT DOCUMENTS

| | | |
|---|---|---|
| 2016/0314580 A1 | 10/2016 | Lloyd et al. |
| 2018/0232883 A1* | 8/2018 | Sethi ............... G16H 30/40 |
| 2019/0388413 A1 | 12/2019 | Nanjundam et al. |
| 2019/0392578 A1 | 12/2019 | Chukka et al. |
| 2020/0286233 A1 | 9/2020 | Chefd'hotel et al. |

FOREIGN PATENT DOCUMENTS

| | | | |
|---|---|---|---|
| WO | 2013/052824 A1 | 4/2013 | |
| WO | 2015/189264 A1 | 2/2015 | |
| WO | 2015/177268 A1 | 11/2015 | |
| WO | WO-2016138041 A2 * | 9/2016 | ......... G01N 33/5011 |
| WO | WO-2018115055 A1 * | 6/2018 | ........... G06K 9/0014 |

OTHER PUBLICATIONS

Janowczyk, A. et al., "Deep learning for digital pathology image analysis: A comprehensive tutorial with selected use cases," J. of Pathology Informatics, 2016, 1:29, 18 pgs.

Extended European Search Report dated Nov. 23, 2020 for European Appn. No. 18763650 filed Mar. 6, 2018, 8 pgs.

Notice of Int'l Preliminary Amend Rpt. On Patentability for PCT Appn. No. PCT/US2018/021060 filed Mar. 6, 2018, 14 pgs.

Non-Final Office Action dated Feb. 25, 2021 for U.S. Appl. No. 16/491,700, filed Sep. 6, 2019, 26 pgs.

Final Office Action dtd Sep. 7, 2021 for U.S. Appl. No. 16/491,700, filed Sep. 6, 2019, 18 pgs.

EPO Communication Article 94 dated Jun. 21, 2022 for EP Appn. No. 18763650 filed Mar. 6, 2018, 6 pgs.

Final Office Action dtd Dec. 29, 2022 for U.S. Appl. No. 16/491,700, filed Sep. 6, 2019, 20 pgs.

Notice of Allowance dtd Jul. 19, 2023 for U.S. Appl. No. 16/491,700, filed Sep. 6, 2019, 9 pgs.

Non-Final Office Action dtd Mar. 24, 2022 for U.S. Appl. No. 16/491,700, filed Sep. 6, 2019, 18 pgs.

* cited by examiner

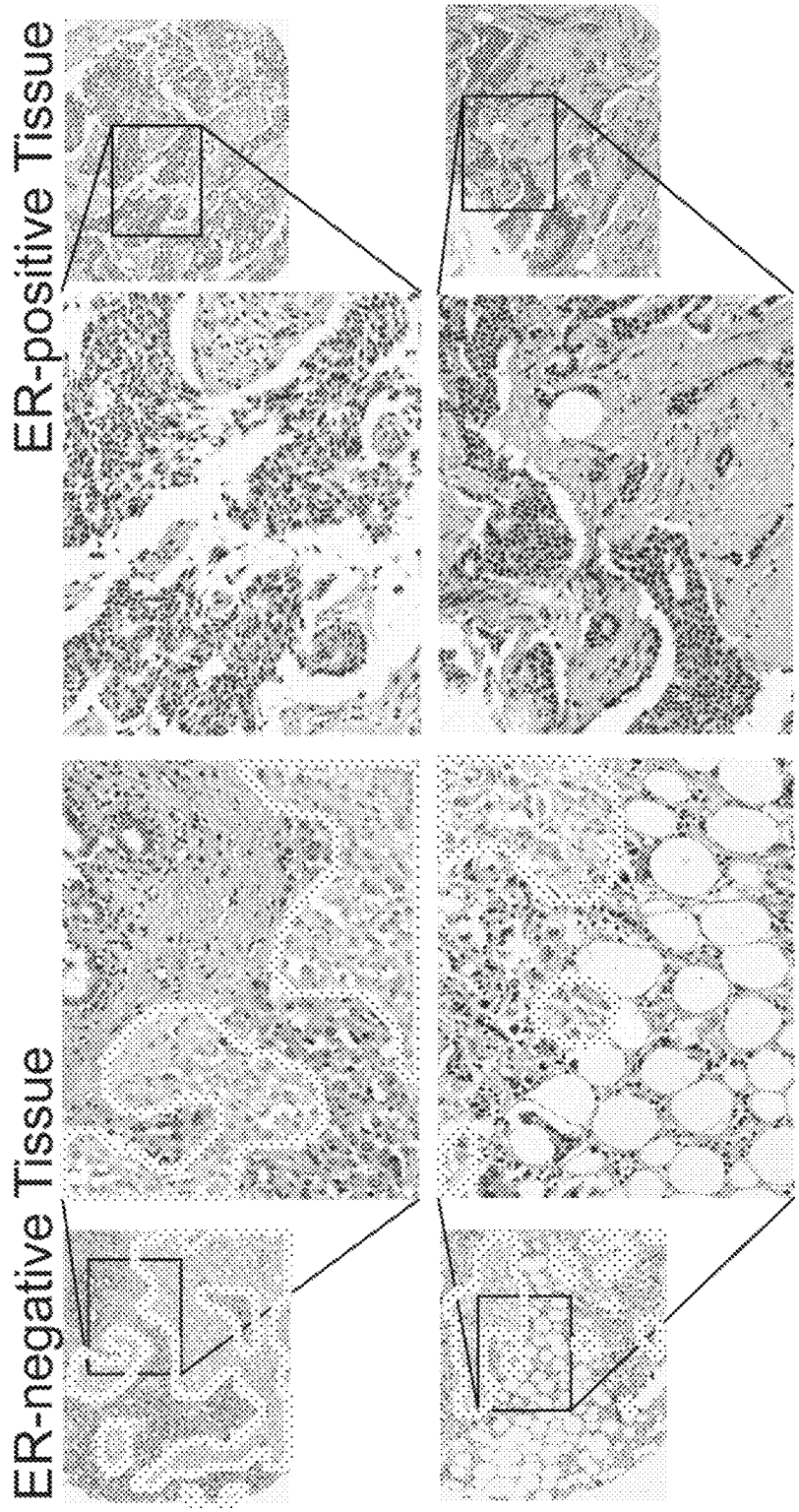

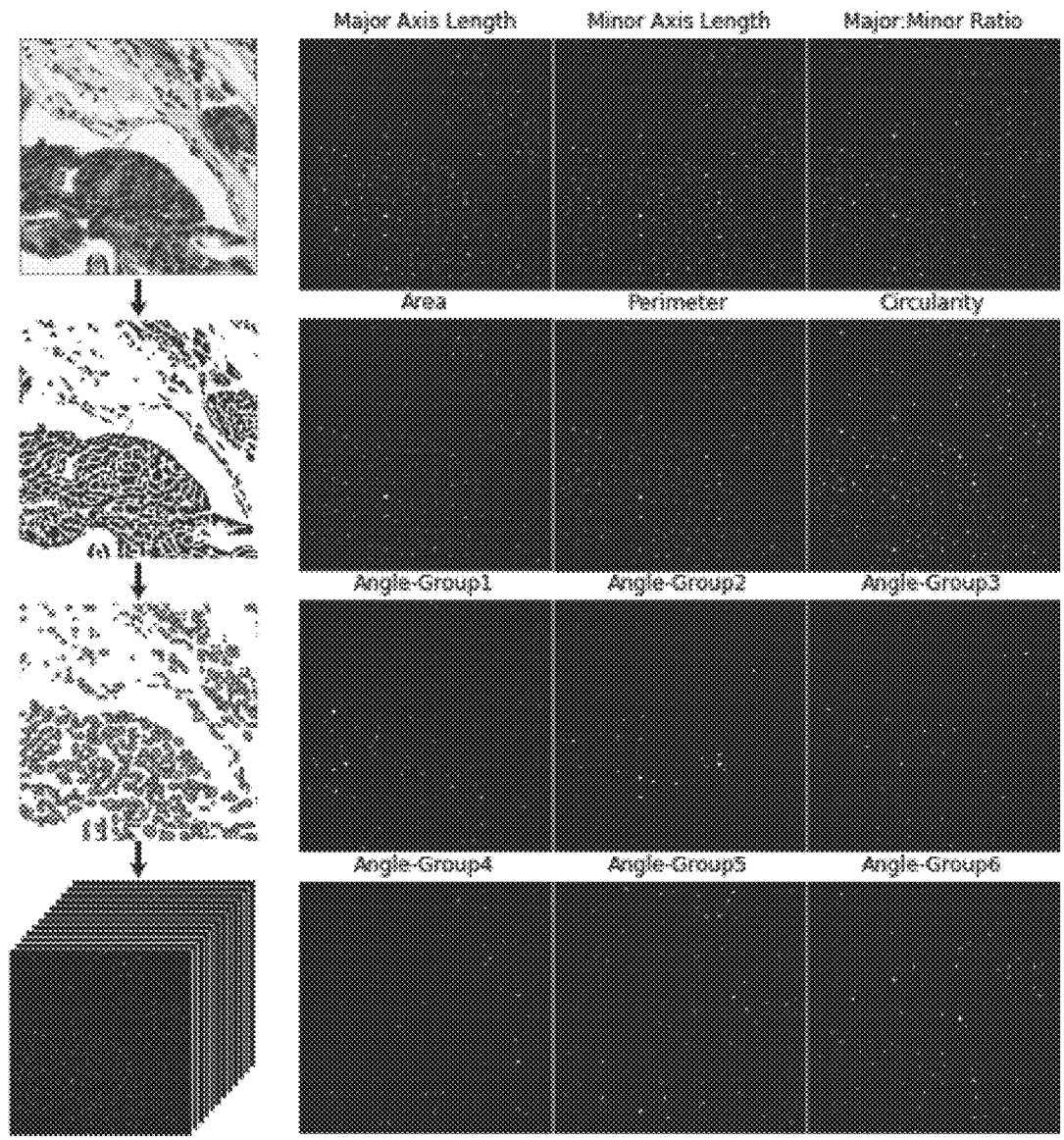
*Fig. 6A*        *Fig. 6B*

MACHINE LEARNING FOR DIGITAL PATHOLOGY

CROSS-REFERENCE TO RELATED APPLICATIONS

This application is a continuation of U.S. patent application Ser. No. 16/491,700 filed Sep. 6, 2019, now U.S. Pat. No. 11,835,524 issued Dec. 5, 2023, which is the U.S. national phase of PCT Application No. PCT/US2018/021060 filed Mar. 6, 2018 which claims the benefit of U.S. provisional application No. 62/467,579 filed Mar. 6, 2017, the disclosures of which are hereby incorporated in their entirety by reference herein.

TECHNICAL FIELD

The present invention, in general, relates to machine methods for diagnosing, theragnosing, and classifying types of cancer.

BACKGROUND

The promise of machine learning in clinical pathology lies in its ability to learn novel, independent patterns that can stratify patients and lead to better clinical decisions. Previous work in digital pathology suggests that hematoxylin and eosin (H&E) images contain a wealth of information that is currently underused in the diagnostic process and may have independent predictive value. For example, computer vision approaches applied to H&E images can detect cancer metastases in lymph nodes[1] and predict survival in lung cancer[2]. Patterns in H&E images may contain diagnostic cues for better diagnosis, stratification and treatment selection. The biology of the cancer is reflected by the patterns and arrangements of the cells, and it has previously been shown by many others that biology of the cancer correlates to clinical outcome and response to therapy. (reference: https://www.cancer.gov/about-cancer/treatment/types/targeted-therapies/targeted-therapies-fact-sheet)

In the US, the standard of care uses multiple immunohistochemistry (IHC) stains and/or molecular tests for estrogen receptor (ER), progesterone receptor (PR), and HER2 to categorize the breast tumor, determine prognosis and select treatment regimens[3,4]. However, these assays may be inconsistent across laboratories[5], and while marker status is predictive of therapeutic response[3,6], the correlation is far from perfect. For example, only 50% of women with ER-positive tumors and 60%-70% of women with ER-positive and PR-positive tumors show partial or complete response to tamoxifen therapy[7,9]. Moreover. IHC stains are similarly used in lung, prostate, brain, and other cancer types.

Accordingly, there is a need for a method of extracting latent information from basic imaging techniques to predict molecular level information that captures the underlying biology of the cancer.

SUMMARY

The present invention solves one or more problems of the prior art by providing in at least one aspect a method assessing tissue morphology using machine learning. The method includes a step of training a selected (i.e., untrained machine) learnable device to predict the status of a diagnostic feature in stained tissue samples. The machine learnable device is trained with a characterized set of digital images of stained tissue samples. Each digital image of the characterized set has a known status for the diagnostic feature and an associated 2-dimensional grid of spatial locations. The training of the machine learnable device includes steps of identifying a plurality of extracted features in each digital image of the characterized set of digital images associating a value for each extracted feature with each spatial location to form a set of extracted feature maps. Each extracted feature map provides values for an extracted feature over the associated 2-dimensional grid of spatial locations. The training also includes a step of inputting the set of extracted feature maps into the machine learnable device to form associations therein between the set of extracted feature maps and the known status for the diagnostic feature thereby creating a trained machine learnable device. The status for the diagnostic feature of a stained tissue sample of unknown status for the diagnostic feature is predicted by obtaining a sample digital image for the stained tissue sample, the digital image having an associated 2-dimensional grid of spatial locations; associating a value for each extracted feature with each spatial location of the digital image to form a test set of extracted feature maps for the stained tissue sample of unknown status; and inputting the test set of extracted feature maps to the trained machine learnable machine to obtain a predicted status for the status of the diagnostic feature for the stained tissue sample.

In another embodiment, a trained machine learnable device formed by the methods set forth herein is provided.

In at least one aspect, the present invention breaks from the current trend in computer vision that incorporates a large number of color, texture and pixel level features. Instead, the present invention focuses on cellular morphology and trained a deep convolutional neural network to learn relationships between nuclear features. Framing the problem in terms of biological units (such as cell nuclei) provides a more natural means to interpret learned patterns than pixel level features, and reduce the impact of noise (such as staining variation) in H&E images.

The learning pipeline described herein is applied to the task of ER prediction in Breast tumors. ER is an important clinical variable as its presence is a strong indicator of response to endocrine therapy[4]. After testing and training the neural network on independent Invasive Ductal Carcinoma (IDC) and Ductal Carcinoma in Situ (DCIS) datasets, it was found that the pipeline can significantly predict ER status (AUC 0.7-0.8) from H&E images. The approach can be scaled to other critical markers such as HER2, cytokeratin, Ki-67, and molecular phenotypes[5] used in current clinical workflows (luminal A, luminal B, basal, and HER2 positive). The approach can also be applied to predict response or survival variables directly, such as 5 Y survival, or days to recurrence following administration of hormonal therapy.

Aspects of the invention that focus on morphometric features provide a unique way to analyze the trained classifier. Analysis of the trained neural network leads to the conclusion that large pleomorphic nuclei are an important feature for distinguishing between ER positive and negative breast cancer tissue. Refinements to this approach can reveal new patterns that distinguish between tissue types.

In another aspect, the deep learning pipeline extracts morphometric features (e.g., nuclear, cytoplasmic, and extracellular morphometric features) from H&E images and feeds them into a deep convolutional neural network[10] to learn spatial patterns, and then uses these patterns to predict ER status. After training the network on an H&E image dataset of invasive ductal carcinoma (IDC)[11], it is found that the trained neural network can predict ER status on a test set of independent patient images of IDC[11] (AUC=0.7) and ductal carcinoma in situ (DCIS)[12] (AUC=0.8). This result highlights the potential for combining expert-defined features (e.g. nuclear properties) with neural networks to predict the molecular biology of a tumor. This framework can be scaled to larger datasets, additional markers (e.g. HER2, progesterone receptor, Ki-67), and molecular phenotypes[13].

In another aspect, the variations seek to predict outcome variables, dependent on tumor biology, such as survival, recurrence, and treatment response and duration directly from morphology.

In another aspect, training the neural network on nuclear morphometric features can provide a way to address the longstanding interpretability challenge of deep neural networks. While deep networks have proven to be remarkably successful at a number of tasks in digital pathology[14], an open problem in artificial intelligence is deconstructing the functions learned by deep networks to determine what the DNN learned. By preprocessing images and extracting expert-defined features (nuclear morphometric properties), the input to the neural network is simplified, and this was found to improve interpretability of the trained network. For example, deconstructing the trained network from this pilot revealed that the DNN learned to correlate large pleomorphic nuclei with ER-negative breast cancer.

In still another aspect, embodiments directly incorporate domain knowledge into the neural network by learning on relevant, pathology-driven features (morphometric features of identified nuclei), rather than forcing the NN to learn these features from raw pixels. In testing alternative approaches, is found that a neural network could not be built based on raw pixel processing on so few samples.

DRAWING DESCRIPTIONS

FIG. 1. Schematic illustration of a method for a method for making diagnosis for stained tissue samples FIG. 2. An idealized schematic illustration of a convolutional neural network FIGS. 3A, 3B, and 3C. A) Receiver operating characteristic (ROC) curves for the IDC-Training dataset (AUC=0.70, 95% CI=0.56-0.85), 3B) IDC-Test dataset (AUC=0.72, 95% CI=0.55-0.89), and 3C) DCIS-Test dataset[12] (AUC=0.81, 95% CI=0.70-0.93).

FIGS. 4A and 4B. Digital stain for regions predicted to be ER-negative. Pixels are enclosed by a dotted line in regions predicted to be ER-negative with probability greater than 50%. Enlarged regions of ER-negative tissue in FIG. 4A reveal that the network classifies sub-regions of epithelial tissue as ER negative. For comparison, ER positive tissue is shown in FIG. 4B FIGS. 5A, 5B, and 5C Correlating nuclear morphometric features with ER predictions from the neural network. Image "patches" were extracted from the IDC-Training dataset, ranked by predicted probability of ER-status, and divided into 15 groups by prediction status. A) Two representative patches classified as ER positive and ER negative are shown. B) The mean of each nuclear feature was calculated within each patch (intra-patch mean); within each group, intra-patch means were averaged to calculate the inter-patch mean. C) The variance of each nuclear feature was calculated in each patch (intra-patch variance); within each group, intra-patch variances were averaged. The x-axis in b indicates group number, higher group numbers correspond to ER negative predictions.

FIGS. 6A and 6B. Construction of a sparse 12-channel image. A) Hematoxylin and eosin stained tissue are processed by a nuclear segmentation algorithm. Each nuclear feature is measured and represented on a single 2D array, where individual cells are represented as points. Arrays are stacked to form a 12D image. B) Detailed view of 12 individual channels that would be stacked to from a 12-channel image.

Figure 7A:
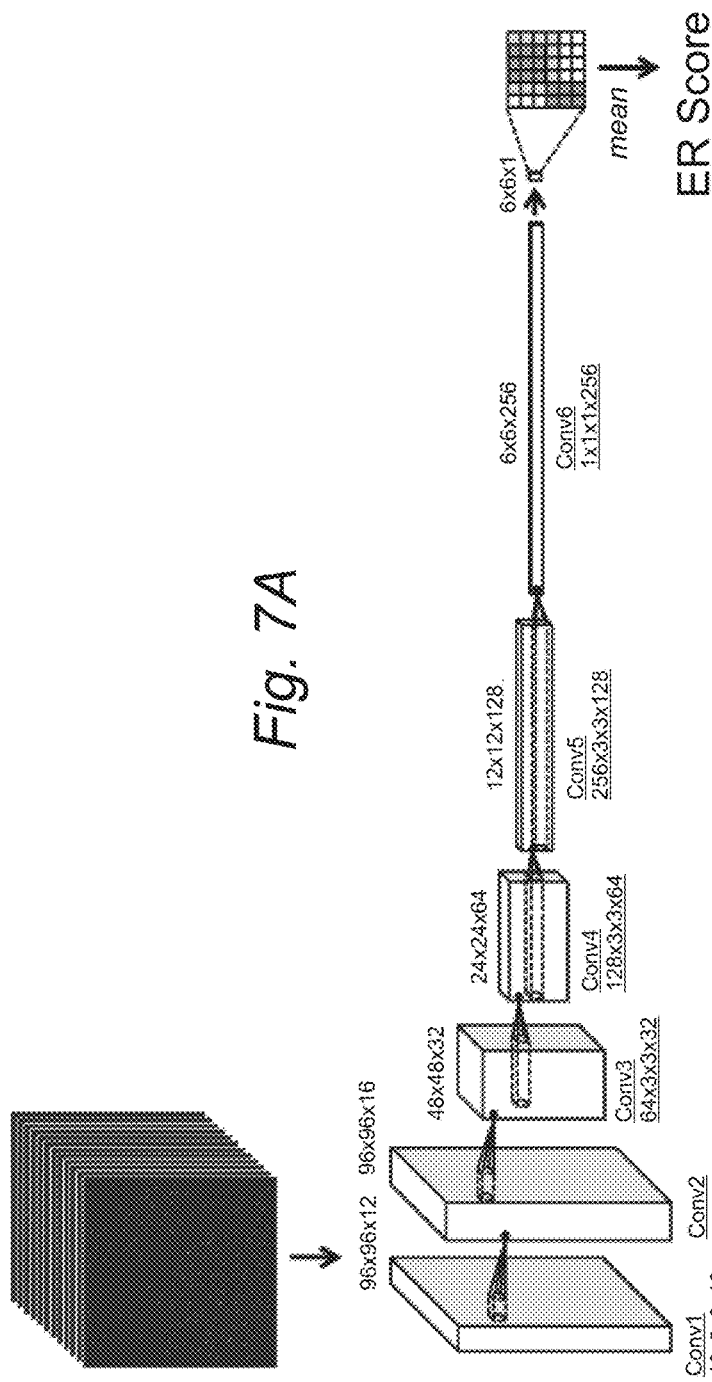
Figure 7B:
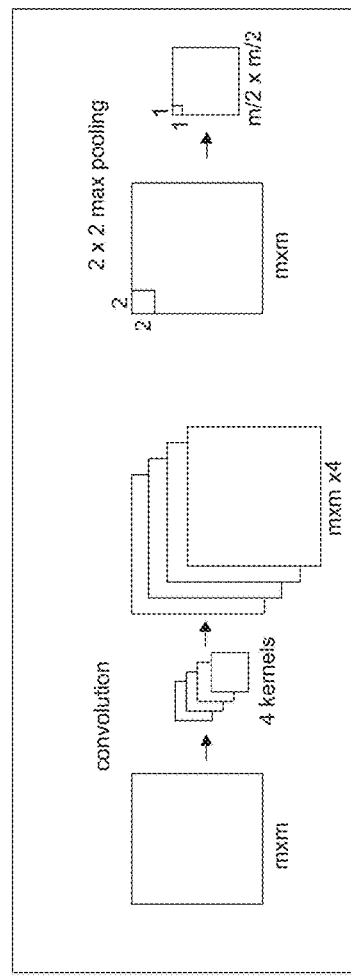

FIGS. 7A and 7B. Schematic of the deep neural network. A) The 12 Channel Image is loaded into a fully convolutional network with six convolutional and max-pooling layers (not shown for simplicity). The output is a 1D map of ER predictions, which is averaged and normalized (not shown) to produce an ER score for the image. The size of the matrix that holds the convolutional weights is indicated by underlining, where a matrix N×C×X×Y has N Kernels that act on a C channel input of size X×Y×C. B) An example of convolutional and max pooling operations. In convolution, the starting image (left) is convolved by four kernels (middle) to produce four feature maps (right). In max pooling, the maximum value of each 2×2 square is used to produce an output image.

Figure 8B:
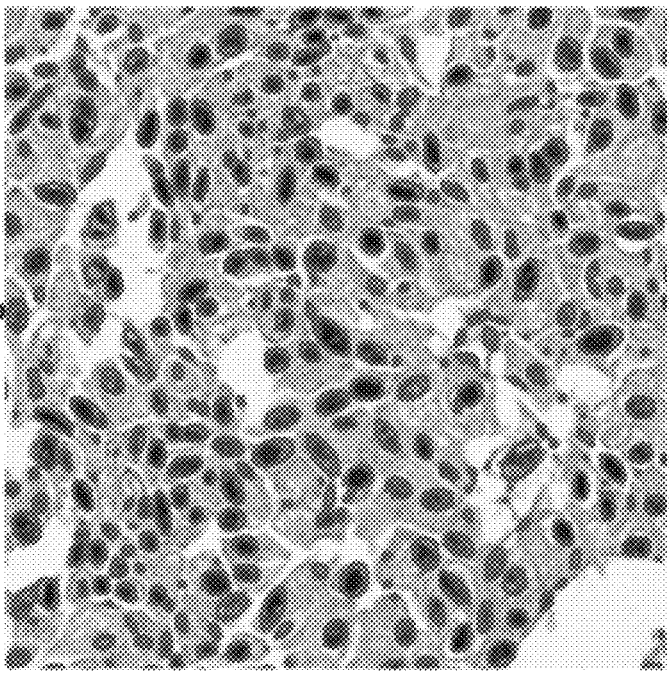
Figure 8A:
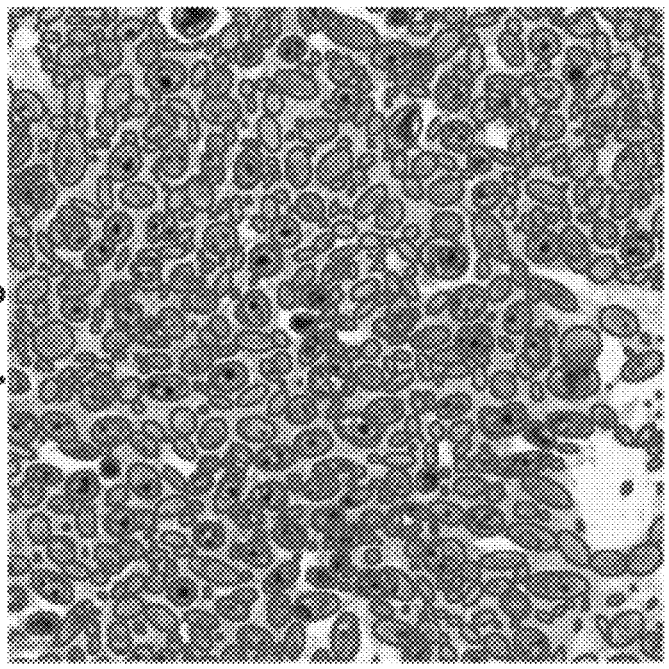

FIGS. 8A and 8B. The neural network was trained using adadelta gradient descent[1] with binary cross entropy loss. Initially, 20% of the training data were held-out for cross validation during the training process (gray) and 80% of the training data were used for training (black). Starting at epoch 825, all training data were used to train and validate the model (black).

Figure 9:
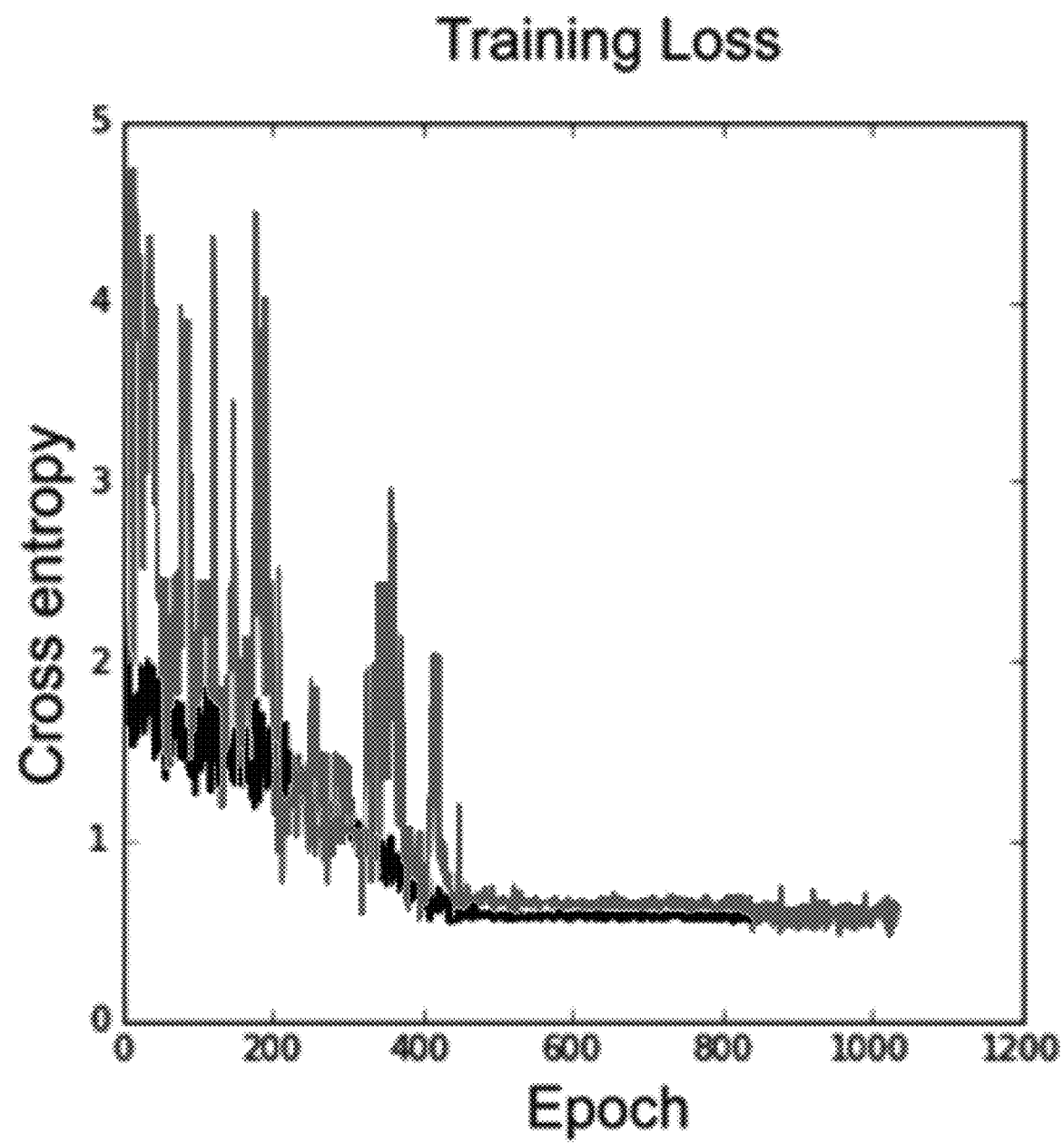

FIG. 9. Exemplary over-segmented and well-segmented images. An image is deemed well segmented if it appears to be greater than 70% concordant.

DETAILED DESCRIPTION

Reference will now be made in detail to presently preferred compositions, embodiments, and methods of the present invention which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

The term "comprising" is synonymous with "including," "having." "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the"

comprise plural referents unless the context clearly indicates otherwise. For example, reference to a component in the singular is intended to comprise a plurality of components.

Throughout this application, where publications are referenced, the disclosures of these publications in their entireties are hereby incorporated by reference into this application to more fully describe the state of the art to which this invention pertains.

Abbreviations

"AI" means artificial intelligence.
"AUC" means area under the receiver operating characteristic curve.
"DCIS" means ductal carcinoma in situ of the breast
"DNN" means deep convolutional neural network.
"ER" means estrogen receptor.
"H&E" means hematoxylin and eosin.
"IDC" means ductal carcinoma.
"IHC" means immunohistochemistry.
"ML" means machine learning.
"NN" means neural network.
"PR" means progesterone receptor.

With reference to FIG. 1, a schematic illustration of a method for a method for making diagnosis for stained tissue samples is provided. The method includes a step a) in which a digital image of a stained tissue sample 12 is obtained. Characteristically, each digital image has an associated two-dimensional grid of spatial locations. In step b), a plurality 14 of extracted feature maps are created from the digital image 10 in a pre-processing step. The extracted features can include morphometric, colorimetric, cell classification and traits, and the like. In this context, "extracted features" refers to features of the stained tissue sample that can be identified and/or verified by a trained professional (e.g, a pathologist or other physician). These expert-selected features can be automatically extracted with image processing algorithms. In step c), machine learnable device 16 receives plurality 14 of extracted feature maps as a pre-processed input. Machine learnable device 16 is trained to predict the status of a diagnostic feature (e.g., ER status, see below for more details) in stained tissue samples. The untrained machine learnable device is trained with a characterized set of digital images of stained tissue samples. Characteristically, each digital image of the characterized set has a "known" status for the diagnostic feature. Machine learnable device 16 executes a machine learning algorithm to determine the diagnostic feature. Examples of such machine learning algorithms include, but are not limited to, neural networks, Bayesian networks, decision tree algorithms, support vector machines, and the like. Particularly useful algorithms for practicing the present invention are neural networks, and in particular, convolutional neural networks. Machine learnable device 16 includes computer processor 20 in communication with random access memory 22. Computer processor 20 executes the machine learning algorithm. Marching learnable device 16 also includes non-transitory memory 24 (e.g., DVD. ROM, hard drive, optical drive, etc.) which can have encoded instruction thereon for producing output 18 from the extracted feature maps using a machine learning algorithm. Typically, the machine learning algorithm instruction will be loaded into random access memory 22 from non-transitory memory 24 and then executed by computer processor 20. Machine learnable device 16 and also include input/output interface 26 that can be connected to displayer 28, keyboard and mouse. When machine learnable device 16 has been trained as set forth below, the status of an unknown sample can be evaluated. In step d), machine learnable device 16 produces output 18 which provides the status for a diagnostic feature of a stained tissue sample. Advantageously, the diagnostic feature can be use make theragnostic, prognostic, and/or diagnostic decisions for a patient.

Figure 2:
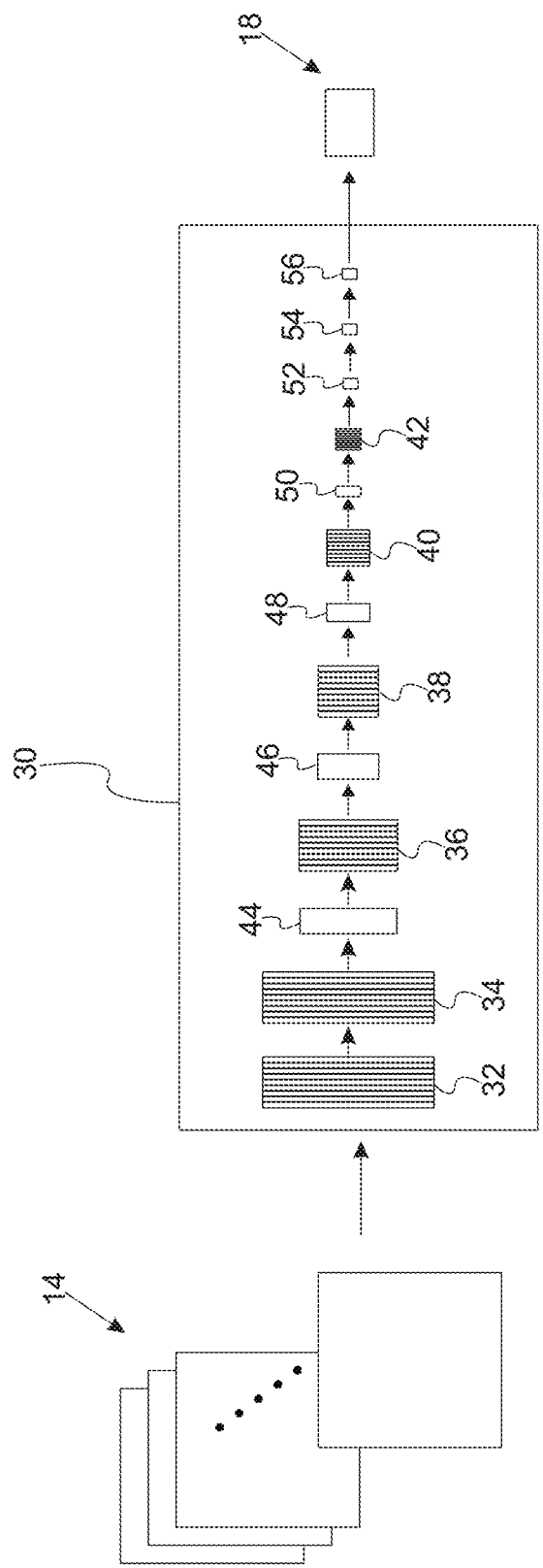
Figure 3A:
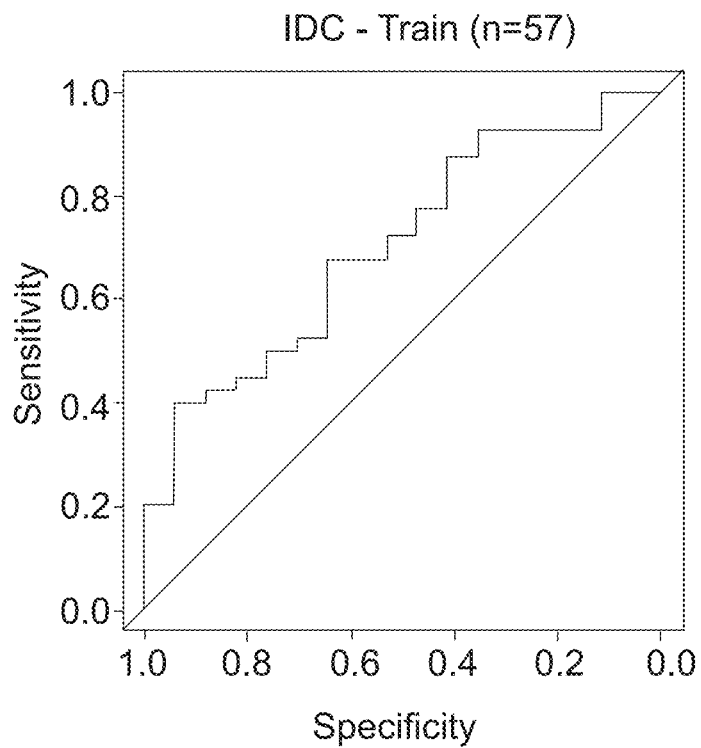
Figure 3B:
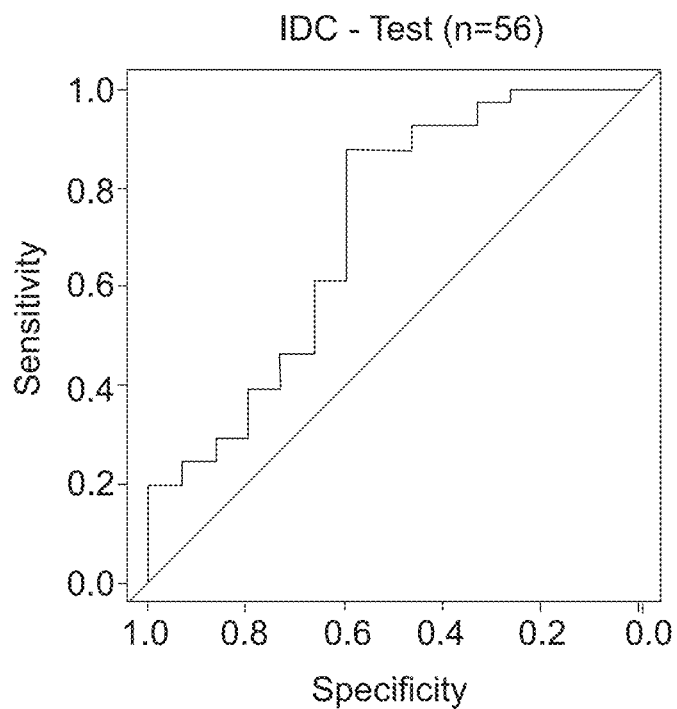
Figure 3C:
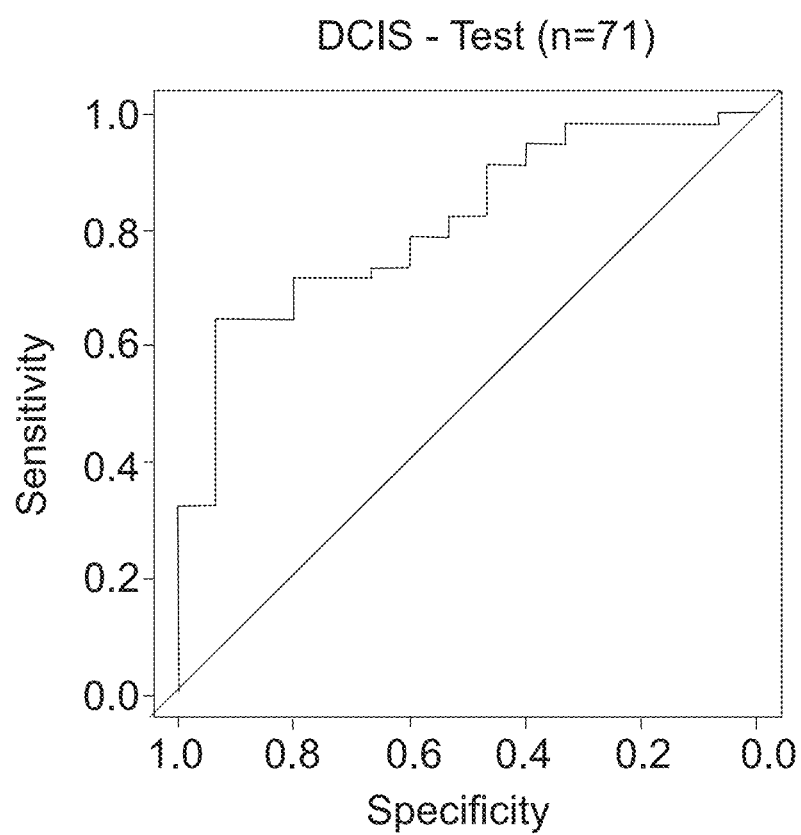

With reference to FIG. 2, an idealized schematic illustration of a convolutional neural network executed by machine learnable device 16 is provided. It should be appreciated that any deep convolutional neural network that operates on the pre-processed input can be utilized. The convolutional network can include convolutional layers, pooling layers, fully connected layers, normalization layers, a global mean layer, and a batch-normalization layer. An alternative setup to using the global mean layer is to combine convolutional layers with a recurrent neural network layers (for example a "long-short-term memory layer" (LSTM)). The recurrent neural network layers could perform a similar function to the global mean layer, in that they can aggregate information from an arbitrarily large image into a fixed length vector. An example of using recurrent neural nets is the following paper: www.nature.com/articles/s41598-018-21758-3; the entire disclosure of which is hereby incorporated by reference. However, the method of this paper acts on raw pixels, unlike ours which acts on pre-extracted features. A global mean layer that takes a feature-wise mean over the entire input matrix results in a fixed-length vector which represents the entire image. Batch normalization, a regularization technique, which may also lead to faster learning. Convolutional neural network layers can be characterized by sparse connectivity where each node in a convolutional layer receives input from only a subset of the nodes in the next lowest neural network layer. The Convolutional neural network layers can have nodes that may or may not share weights with other nodes. In contrast, nodes in fully-connected layers receive input from each node in the next lowest neural network layer. For both convolutional layer and fully connected layers each node calculated its output activation from its inputs, weight, and an optional bias. During training, optimal values for the weight and bias are determined. For example, convolutional neural network 30 receive plurality 14 of extracted feature maps as a multichannel image. Convolutional neural network 30 include convolution layers 32, 34, 36, 38, 40, and 42 as well as pooling layers 44, 46, 48, 50 and 52. The pooling layers can be max pooling layer or a mean pooling layer. Another option is to use convolutional layers with a stride size greater than 1. FIG. 2 also depicts a network with global mean layer 54 and batch normalization layer 56. Each of the convolution layer can include multiple internal feature maps which can change from layer to layer via subsampling and convolution. The present embodiment is not limited to by number of convolutional layers, pooling layers, fully connected layers, normalization layers, and sublayers therein.

The methods set forth herein advantageously uses deep learning to extract information from stained tissue samples. In general, we show that deep learning is powerful and interpretable if it is applied on a matrix of expert-defined medium-level features. In the prior art, the deep learning systems learn medium-order and high-order relationships directly from low-level features such as the actual RGB pixel values. In some cases, this approach of learning directly from RGB pixel values works well because neural networks are good at learning spatial relationships between inputs. In cases where there are enough accurately annotated data, pixel-based deep learning can be a good strategy for building an accurate classifier. However, in medicine/pathology, it is difficult to get enough labeled data of sufficient quality. Moreover, there is a strong desire by physicians to get an intuitive idea of the features that the deep neural network uses to make a classification of diagnosis, prognosis or theragnosis. So instead of traditional approaches which use the raw pixel inputs, embodiments of the present invention perform a pre-processing step that extracts a set of medium-level features that are defined by humans, and can be verified by humans (e.g. the nuclear morphometric features).

In this regard, a human can first confirm that the input (the pre-processed features) to the deep neural network meets some minimal quality threshold. For instance, a quality control step can be performed to make sure the quality of the input feature maps (FIG. 2, item 14) to the deep neural network is sufficient. This is important because a major potential risk in deep learning is that the neural network learns relationships that represent artifacts in the data, rather than real biologic changes. After the preprocessing-step step is done, a human can perform a quality control check to ensure that the data that enters the neural network reflects basic biological assumptions. For instance, it is well known that H&E staining of two consecutive sections can result in images that look vastly different on the color spectrum just by differences in the concentration of dyes used to produce the image. The color variations are an example of noise and may bias neural networks to perform differently on samples processed in different laboratories (due to different stains in different laboratories). Extracting a predefined set of features that are considered robust to common variations in preparation methods such as nuclear morphometry is a way to normalize and regularize the data that are fed into the deep neural network.

Although it might be suggested that the pre-processing step results in heavy information loss (e.g., discarded color and texture information), such information loss can be alleviated by adding additional morphometric features in the pre-processing step. Practically, any feature that can be identified reproducibly by a pathologist can be encoded into the described sparse matrix representation. Moreover, if enough morphometric features are extracted and included in the feature maps, the information content in the sparse matrix representation should capture a large quantity of the information content present in the original histopathology image. Thus, this approach does not necessarily lead to a loss of information compared to using the raw pixel input.

Alternatively, it may be useful to purposefully restrict the types of morphometric features that are extracted and utilized to understand the predictive value of these features independent of other features. For instance, comparing the classification results of a deep neural network trained on nuclear morphometric features to a deep neural network trained on cytoplasmic and extracellular morphometric features can provide intuition about which morphometric features are most predictive of an outcome.

Another benefit of limiting the input data to a subset of pre-extracted morphometric features (e.g., nuclear morphological features) instead of the original RGB pixel value images is that it allowed the deep neural network to learn a function that generalized to the test set with a statistically significant AUC (Invasive Ductal Carcinoma AUC=0.72, 95% CI=0.55-0.89, n=56; Ductal carcinoma in situ AUC=0.81, 95% CI=0.70-0.93, n=71). For example, on the same dataset that was tried training on the raw pixel level, it was found that the neural network over-fit the training set and did not generalize to the test set. Thus, performing the morphometric pre-processing step might force the deep neural network to learn biologic relationships rather than spurious relationships.

The neutral networks that are most useful use the following general design paradigm: a series of convolutional layers, which learn hierarchical spatial relationships (first learn relationships between objects close to each other, then relationships between those objects). The outputs of the convolutions are fed into a fully connected layer (or a fully convolutional layer, which serves a similar purpose), which learns combinations of spatial relationships and outputs a prediction. Importantly, looking at any one portion of an image may not be sufficient to make an accurate prediction. It is important to be able to combine information from multiple parts of an image to make a classification for the patient. Thus, a global pooling layer or pooling mechanism which aggregates outputs from multiple portions of the image is important. Overall, the key elements of the neural network processing used herein include: local computation to capture spatial relationships of cells/nuclei/extracellular matrix components near each other. Then more computation to integrate features from larger areas. Finally, a method to combine information from multiple portions of an image.

As set forth above, the training of the machine learnable device 18 includes a step of identifying a plurality of extracted features (e.g., morphological features) in each digital image of the characterized set of digital images. In a refinement, the extracted features are morphological features that describe shape, texture, and color of cellular and/or sub-cellular components. Morphological features include nuclear, cytoplasmic, and extracellular (extracellular matrix morphometry descriptors) morphological features. Examples of such cellular and/or sub-cellular components include, but are not limited to, individual cells, mitotic figures, cell nucleus, vacuoles in the cytoplasm, extra cellular space, and nucleolus. In another refinement, the extracted features include colorimetric features within a structured biologic element. A value for each extracted feature is associated with each spatial location to form a set of extracted feature maps. Therefore, there will be a two-dimensional feature map for each extracted feature used in the present method. For example, if there are 12 extracted features being used, the digital image of a tissue sample being analyzed will have 12 associated feature maps. Each extracted feature map provides feature values for a extracted feature at each point of associated two-dimensional grid of spatial locations. It should be appreciated that these feature values can be a single number, a vector or a matrix. The set of extracted feature maps (i.e., the feature values with associated position coordinates) is inputted to the machine learnable device to form associations therein between the set of extracted feature maps and the known status for the diagnostic feature to form a trained machine learnable device.

The machine learnable device 18 having been trained in this manner can now be used to make predictions regarding tissue samples with an unknown status for the diagnostic feature. In particular, a status for the diagnostic feature of a stained tissue sample of unknown status for the diagnostic feature is predicted as follows. A sample digital image for the stained tissue sample is obtained. As set forth above, the digital image has an associated 2-dimensional grid of spatial locations. A feature value for each extracted feature is associated with each spatial location of the digital image to form a test set of extracted feature maps for the stained tissue sample of unknown status. The test set of extracted feature maps is inputted to obtain a predicted status for the status of the diagnostic feature for the stained tissue sample.

As set forth above, the methods of the invention predict the status of a diagnostic feature. Typically, this status of the diagnostic feature will be the presence or absence of a biomarker. In one variation, the stained tissue sample is a putative breast cancer sample with the biomarker being selected from ER, HER2, PR, Ki67, and cytokeratin markers. Advantageously, the biomarker can be ER which alone can be used to determine specific treatments (e.g., hormonal therapy). In another refinement, the biomarkers ER, PR, and HER2 are prognostic. For example, patients with ER+ PR+ HER2− have the best outcomes, followed by patients with ER+ PR− with patient having ER−PR− having the worst prognosis. All three markers (i.e., ER, PR HER2) can be used to clarify the cancer and make determinations for treatment. In still other refinements, the biomarker can be E-cadherin and/or PIK3CA with the predicted status being used to differentiate between subtypes of breast cancer (e.g., ductal and lobular carcinoma in situ).

In another variation, the stained tissue sample is a putative cancer (e.g. lung cancer) sample. In this variation, the biomarker can be EGFR, KRAS, c-Met, MET, and ALK. In this regard, Alk rearrangements are theragnostic with specific treatments being known for patients with ALK rearrangements.

In still other variations, the biomarker can be selected from the group consisting of p53 (multiple cancers), Bcl-2 (leukemia), and c-Myc (lymphoma).

As set forth above, a plurality of extracted features, and in particular, a plurality of morphological features is used to characterize each digital image. In this regard, features describing the shape, texture, and color of sub-nuclear components of a cell are important. Examples of such cellular and/or sub-cellular components include, but are not limited to, individual cells, mitotic figures cell nucleus, vacuoles in the cytoplasm, extra cellular space, and nucleolus. These structures are visible on H&E images and can be quantified by shape and color intensity much like the nucleus. Examples of the morphological features that can be used to characterize these components include, but are not limited to, one or more features selected from the group consisting of area, perimeter, circumference, fractal dimension, Zernike moments, mitotic figure, and combinations thereof. In some circumstances, it may be useful to approximate the cellular and/or subcellular components by an ellipse. When such an approximation is made, the morphological features may include one or more features selected from the group consisting of ellipse area, ellipse major axis length, ellipse minor angle length, ellipse angle from horizontal, and combinations thereof.

In another variation, the plurality of extracted features includes color parameters. In particular, color information may be used to quantify cellular and subcellular components. These features are calculated from color channels (either RGB channels or a transformation of these channels (e.g. after color deconvolution)). For example, color related features may include: the mean and variance in color channels throughout the nucleus; the mean and variance in color channels within a radius (e.g. 2 μm) about the nucleus (this is a way to quantify the cytoplasm); the mean and variance in color channels outside cells and throughout the stroma. The difference between using the colorimetric parameters in the present variation and using RGB pixels is the colorimetric parameters describe the colors within a structured biologic element ("cells" or within "nuclei"). They are not raw color pixels of an image.

In still other variations, the identification of extracted features can include a higher-level classification step which may also lead to useful features for machine learning. For example, a useful feature might be the categorical classification of nuclear cell type: epithelial, fibroblast, lymphocytic, myocontractive, and the like.

In still other variations, the extracted features can also include the spatial neighborhood of nuclei and cells. Examples of such features include the number of neighbors within a given radius that satisfy some criteria (e.g. nearest neighbors within 50 micrometers that have a radius >5 micrometers) and the number of white pixels within a radius. It should be appreciated that white pixels may result from various phenomena, such as artifact during tissue processing, fat cells, or spaces between extracellular matrix proteins. Therefore, white pixel quantification contains a wealth of important information about the architecture of a tissue.

In yet another variation of the methods set forth above, further includes steps of determining treatment for a subject from the subjects' predicted status for the status of the diagnostic feature and then treating the subject. Treatment of cancer patients is dependent on the biology of the cancer. The premise of the current invention is that the biology is described in the tissue morphology. Thus, the tissue morphology as assessed by the machine learning methods, can be used as a theragnostic agent in cancer patients to help chose appropriate treatment. An example would be to segregate hormone receptor positive breast cancer patients by morphology using AI/ML, which would then predict outcome to hormone receptor targeted therapy. A logical extension would be to correlate with clinical outcome to targeted therapy (i.e., duration of response and other parameters) that are not associated just with hormone receptor positivity (but may be correlated to associated morphology). In a refinement, the subject can be treated with an appropriate chemotherapeutic agent specific to (i.e., known for the treatment of) the identified status of the diagnostic feature.

The following examples illustrate the various embodiments of the present invention. Those skilled in the art will recognize many variations that are within the spirit of the present invention and scope of the claims.

Nuclear Morphometric Features Predict ER Status in IDC Tissue

Publicly available H&E images and corresponding clinical ER status (positive/negative, determined by IHC) were obtained for 131 invasive ductal carcinoma (IDC) patients on a tissue microarray[11]. After segmenting nuclei and applying a quality control step to exclude over-segmented images (FIG. 8), the images were randomized into a training set ("IDC-Train", 57 patients) and a test set ("IDC-Test", 56 patients). Nuclear morphometric features (shape and orientation) were extracted from each nucleus in the training set. These measurements were fed into a deep convolutional neural network (DNN) to learn spatial patterns that correlate to ER positive or ER negative status. The DNN was designed to produce a spatial heatmap of ER-positive or negative status. When an input image is fed into the DNN, the output is a heatmap of predictions where intense regions correspond to ER-negative status. The overall ER-status prediction for a patient is the average value of the heatmap.

After training the neural network, the pipeline was evaluated on the test set and measured area under the curve (AUC) scores of 0.70 (95% CI=0.56-0.85) and 0.72 (95% CI=0.55-0.89) on the IDC-Train and IDC-Test datasets, respectively (FIG. 3). This result suggests that the pipeline indeed learned to predict ER status from H&E images. Moreover, the similarity between the AUC scores on the training and test sets suggests that the pipeline learned a classification function that generalizes well and does not over fit the training data.

Trained Neural Network Can Also Predict ER Status in Ductal Carcinoma In Situ

Studies suggest that ER status may be an important marker for subtypes of DCIS with different outcomes15,16. To characterize how the patterns learned by the network generalize across subtypes of breast disease, a second publicly-available and previously published dataset ("DCIS-Test")12 consisting of H&E images from patients with ductal carcinoma in situ was obtained.

Following the segmentation and quality control steps, the previously trained network was on images from 71 patients with ductal carcinoma in situ and obtained a statistically significant AUC score of 0.81 (95% CI 0.70-0.93, FIG. 3). Together, these findings suggest that the pipeline learned patterns that correlate with ER in both IDC and DCIS A Correlation Between Nuclear Size, Heterogeneity, and ER Status While deep networks are typically considered to be uninterpretable "black boxes," several techniques were applied to reverse-engineer the system and understand the morphometric patterns the DNN used to classify ER status. The first step was to visualize the heatmap the DNN learned to predict. This analysis is similar to laying an IHC image over an H&E image; however, while an IHC image shows the real protein expression, the DNN heatmap shows regions estimated by the DNN to be ER positive or negative. Because the DNN was trained to predict an accurate patient-level classification (not the spatial pattern of ER-staining), the regions predicted on the heatmap may be different from regions predicted by IHC. However, regions on the DNN heatmap contain information that leads to an accurate ER+/− prediction, and are thus diagnostic regions for ER-assessment.

For this analysis, several cases were selected that were classified correctly and overlaid the predicted heatmaps on the H&E image to form a "digital stain" where ER-negative regions are enclosed by a dotted line and ER-positive regions are uncolored (FIG. 4). By visual inspection, it was observed that a subset of epithelial areas was predicted ER-negative. Thus, it appears that features in epithelial regions are used by the DNN to classify ER status.

Next, the DNN was used to gain intuition about the specific nuclear features linked to the ER prediction. The training images are divided into small image patches (100× 100 pixels, 200×200 μm, approximately 104 total). The ER score for each patch was predicted and sorted the patches by prediction from ER positive to ER negative. Looking only at the extremes (patches most strongly predicted to be ER positive or ER negative), a difference in nuclear size and the variation in nuclear features was noted (exemplary patches in FIG. 5A).

Figure 5A:
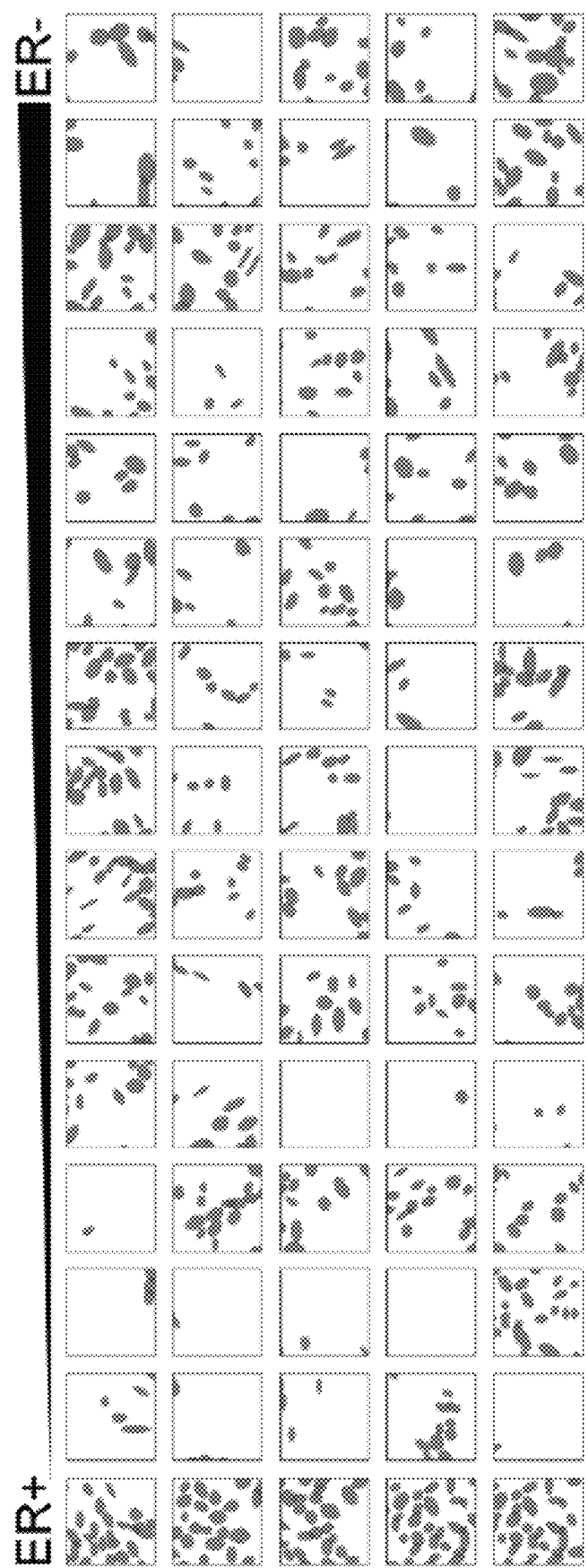
Figure 5B:
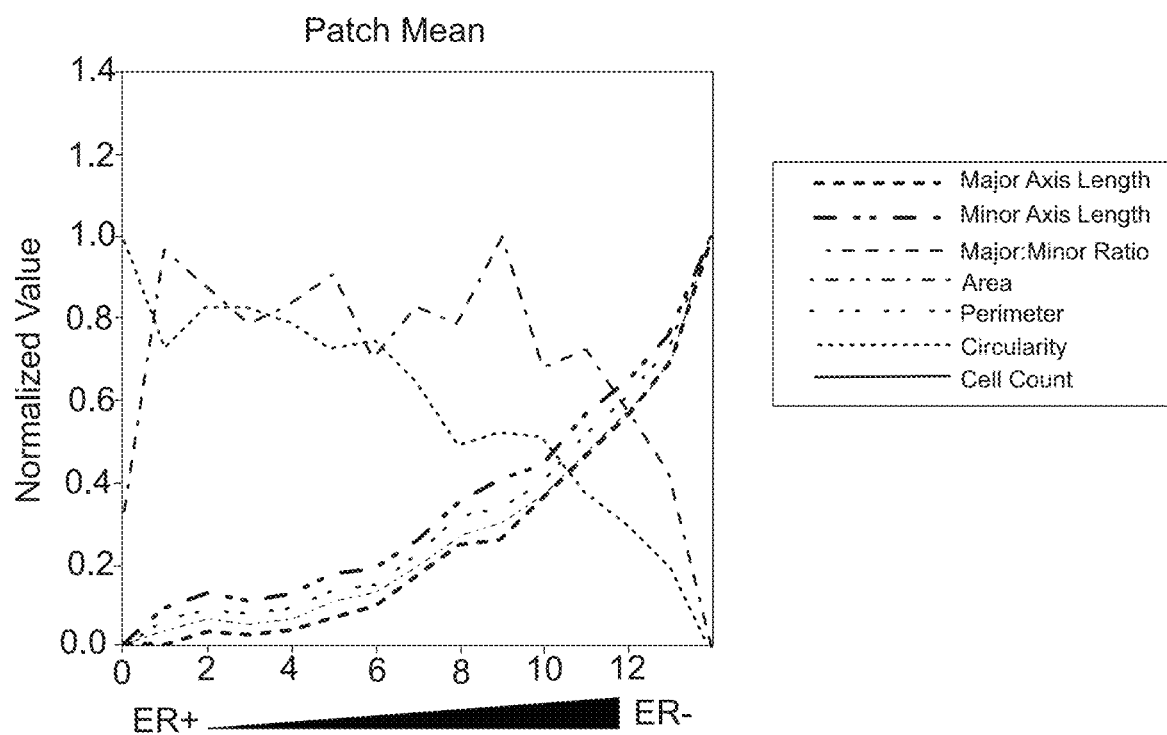
Figure 5C:
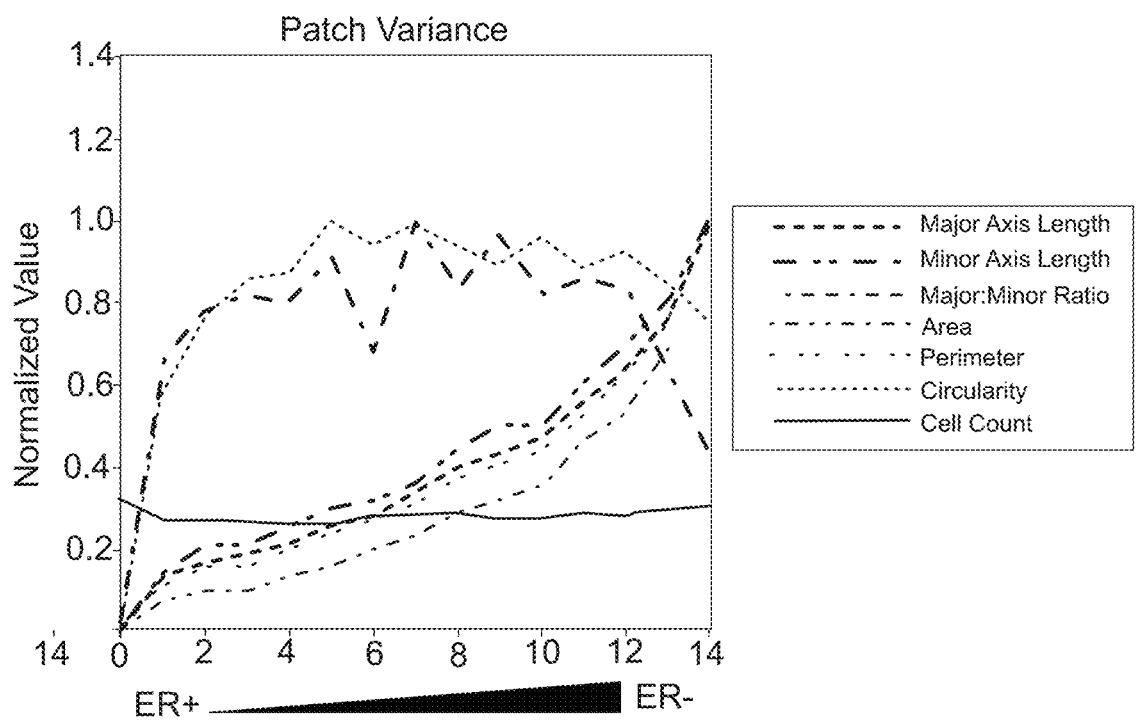

It is hypothesized that the pipeline learned to predict ER status as a function of nuclear size and pleiomorphism. To formally investigate this pattern, the sorted list of patches was dived into 15 groups ranked by predicted ER score. For each patch, the mean value of each nuclear feature (intra-patch mean) and the variance of the feature (intra-patch variance) was calculated. The inter-patch mean and standard error across all patches in the group was also calculated (FIG. 5B). This revealed that several nuclear morphometric quantities, such as mean height, width, area and perimeter were elevated in patches classified as ER negative. Additionally, nuclear heterogeneity (variance of nuclear features) is correlated to an ER negative prediction.

Based on these observations, it was directly tested if the mean and variance of nuclear features in a patch could predict ER status. 5000 patches were randomly from the IDC-Train dataset, calculated the intra-patch means and variances of nuclei within each patch and trained a logistic regression model on these features. Next, the trained logistic regression model was applied to full-sized images in the IDC-Test dataset. Each image was divided into equally-spaced non-overlapping patches, calculated an ER score for each patch, and averaged the ER score from all patches in each test image. On the IDC-Train dataset, an AUC of 0.648 (95% CI: 0.498-0.799) was obtained. On the IDC-Test dataset, an AUC of 0.6715 (95% CI: 0.494-0.850) was obtained. While these linear classifiers are less accurate than the DNN, the trend suggests that these features capture information about ER status. Analyzing a DNN trained on expert-defined features helped us interpret the DNN in terms of biological relationships.

Together, these findings suggest that nuclear morphometric features can be used to predict the presence of the estrogen receptor. A neural network trained on IDC images predicted ER status on a held-out IDC dataset (IDC-Test) and an external DCIS dataset (DCIS-Test). Further analysis of the trained neural network suggests a biological difference between ER positive and negative tissue: large, pleomorphic nuclei seem to be correlated with an ER negative prediction.

DISCUSSION

Embodiments herein aim to determine whether tissue morphology reflects the biologic state of hormone receptor signaling pathways in breast cancer samples. Using deep learning and labeled tissue images, a learning pipeline to correlate patterns of nuclei to ER status was trained, based on IHC staining as the reference. Analysis of the trained model revealed that the morphometric-biologic correlation is dependent on the association of large pleomorphic nuclei with ER negative tumors. This is the first work to use deep learning to identify, correlate, and explain how a morphologic pattern in a pathology image correlates to signaling pathways reflecting the underlying molecular biology of a cancer. Future studies will correlate to clinical responsiveness to ER pathway therapeutics.

A core factor in this work was the development of a hybrid machine-learning approach that combined expert-defined local features with the powerful feature-learning framework of convolutional neural networks. While convolutional neural networks can learn high-order features from the raw image data, training these models typically requires thousands to millions of training images to minimize the impact of noise and color variations. Limited by the quantity of annotated training images, variations of the invention introduced a pre-processing step to extract nuclear morphometric data and developed a novel method for deep learning on these features instead of the raw RGB image pixels, which may be subject to H&E staining variation. Preprocessing effectively compressed each training image into a vector of morphometric data. While this constrains the types of features the neural network could learn, it also prevents it from learning spurious correlations between nonsensical variables (e.g., staining variation). Thus, it is believed believe using expert-defined features as input allowed the network to learn patterns that generalized well between the training and test datasets and between IDC and DCIS images.

The network's performance on the DCIS dataset was intriguing. While the network was trained on IDC images, the high accuracy on DCIS images may be explained by a several factors. Biologically, it has been noted that there are morphometric similarities between DCIS and IDC17, thus patterns learned on IDC may apply to DCIS. Another explanation is that the co-occurrence of DCIS and IDC in some of the IDC training images allowed the network to learn patterns for DCIS and IDC simultaneously. An alternative explanation is that the higher accuracy on the DCIS dataset was due to the method of dataset preparation. Images in the DCIS dataset were carefully chosen by pathologists and contain little stroma relative to epithelial tissue. On the other hand, images in the IDC datasets were obtained from a commercial tissue microarray supplier. These cores are large, diverse (containing a mixture of stromal and epithelial tissue), and noisy (exhibiting varying degrees of staining artifact). Thus, biologic or region-selection factors may explain the accuracy on the DCIS dataset.

The promise of machine learning lies in its ability to learn novel, independent patterns that can stratify patients and lead to better clinical decisions. While previous works in digital pathology have suggested that H&E images contain a wealth of information that is currently underused in the diagnostic process, variations of the invention demonstrate that the information contained in the shapes and arrangements of the nuclei contain information that is correlated to the molecular biology of breast cancer. While this pipeline can be adapted and scaled to classify other subtypes of breast cancer, breast cancer markers, molecular phenotypes13 (luminal A, luminal B, HER2, basal), etc, the power of the inventive approach lies in the ability to extract biological insights from the neural network. The hybrid system is not a "black-box" learning system. It learns high-order features based on lower-order, human-defined features that can be reverse-engineered to gain intuition about biology. In embodiments of the present invention, digital staining and patch analysis was used to learn the correlation between large pleomorphic nuclei with ER negative tumors.

Method

It is hypothesized that the combination of (1) spatial arrangement of cells combined with (2) nuclear morphometric properties would capture important information about the underlying molecular biology of breast cancer and provide clinically useful predictions. Thus, a learning pipeline was constructed to classify cancers by molecular markers. Here, this hypothesis was tested on the pathological classification of a tumor as ER+ or ER−. The method comprises five steps: (1) data acquisition, (2) image pre-processing, (3) quality control, (4) designing and training the neural network and (5) testing the neural network.

Step 1: Data Acquisition

Dataset 1: IDC

The first set of acquired H&E images were from the website of the tissue microarray supplier, US Biomax, Inc. (Derwood, MD 20855). As a service to customers, US Biomax, Inc. provides JPEG-compressed H&E images of many tissue microarrays along with immunohistochemistry (IHC) staining information, such as ER receptor status. With permission from US Biomax, Inc., the array titled "HBre-Duc140Sur-01" (www.biomax.us/tissue-arrays/Breast/HBre-Duc140Sur-01) was used, which contains 140 tissue cores (1.5 mm diameter) from 140 patients diagnosed with invasive ductal carcinoma. This particular microarray was chosen because the H&E images displayed minimal staining artifacts and included molecular marker staining status. To collect the data, the digital slide viewer was used on the US Biomax, Inc. website, zoomed in to 20× resolution (0.5 μm per pixel) with screenshots taken of each core. These images were correlated to ER status (from the US Biomax, Inc. website), and then fed into the pre-processing pipeline. Following a quality control step (described below), 113 tissue cores remained, with one core per patient. These patients were randomly divided into the "Biomax training" (n=57) and "Biomax test" (n=56) datasets.

Dataset 2: DCIS

A second dataset (called "DCIS") consisting of H&E images with ER status for patients with ductal carcinoma in situ was used. The DCIS dataset is a subset of a publicly available dataset12 that contains 327 H&E images for 167 patients with either ductal carcinoma in situ or usual ductal hyperplasia (UDH). ER status was not available for patients with UDH. Out of the patients with ductal carcinoma in situ, ER status was available for 84 patients. Out of these 84 patients, 71 patients passed the quality control step (described below) and were included in the DCIS dataset. The original image resolution in the DCIS dataset is 40× (0.25 μm per pixel). These images were rescaled to be the same resolution as the Biomax dataset (0.5 μm per pixel) using bicubic sampling before subsequent processing steps. The DCIS dataset was used as an external validation dataset. Table 1 summarizes the IDC and DCIS datasets.

Step 2: Image Pre-Processing

A fully automated nuclear segmentation pipeline using Python (version 2.7.12) and Fiji18 (version 1.0, a distribution of ImageJ19) was. The steps consist of the following:
  Scale images as necessary to a resolution 0.5 μm per pixel, using bicubic interpolation.
  Transform the RGB image into hue, saturation, brightness channels, retaining only the brightness channel for downstream analysis.
  Apply an automatic, global Otsu threshold20 to roughly identify cellular regions
  Apply a local adaptive threshold with a radius of 20 pixels (10 μm) to provide fine-scale local separation of nuclei.
  Use the built-in Fiji watershed transform to separate overlapping nuclei.
  Calculate the following morphometric parameters for each detected nucleus using the particle analysis functions in Imagej: center of nucleus (x, y coordinates), major axis length, minor axis length, major axis to minor axis ratio, area, perimeter, and circularity.
  Convert data into a MultiCellDS digital tissue snapshot (a standardized XML representation for spatial multicellular data)21 for storage.
  The pre-processing image scripts are available in the supplementary materials.

Step 3: Quality Control

A label-blind quality control step was performed in which 200×200 pixel patches were extracted from each H&E image and overlaid with ellipses representing the extracted nuclei. Visually, RR assigned a Boolean value (0 or 1) to each image corresponding to whether the image appeared well segmented (defined as greater than 70% concordant, Supplemental FIG. 3). Patients with unknown ER status were excluded from the analysis. As a result of the quality control step, 113 out of 140 cases were used from the IDC dataset and 71 out of 84 ductal carcinoma in situ cases for the DCIS dataset.

Step 4: Designing and Training the Neural Network

Each MultiCellDS digital tissue snapshot was converted into a sparse 12 channel image (FIG. 6), consisting of zeros everywhere except at the cell centers, which contain information about the nuclei. The first six channels correspond to cellular shape features (major axis, minor axis, major:minor ratio, area, perimeter, circularity). In addition, 6 "binary angle" features from the nuclear angle measurement were constructed, leading to a total of 12 feature channels; if the major axis of cell i has an angle $\theta i$ ($0<\theta i<180$) with the positive x-axis, six orientation features $\varphi i, j$ ($1 \le j \le 6$) are defined by $\varphi i, j = 1$ if $30 \times (j-1) < \theta\_i \le 30 \times j$ $\varphi i, j = 0$ otherwise.

The rationale for constructing binary features relates to the training process for the neural network. It was desirable that the network learn rotationally invariant features, which are robust to flips and rotations (in the spatial image coordinates) of the 12-D image. Using binary angle channels allowed us to flip or rotate the image while keeping the cell angle information properly oriented.

The final step before training involved downscaling the sparse images 4× via nearest-neighbor scaling to reduce downstream computation. Thus, the DNN sees cell features at a resolution of 2 μm per pixel. Following down sampling, cells positioned at physical coordinates (x1, y1), are positioned at matrix indices (x2, y2) such that:

$x2 = \text{floor}(x1/4)$ $y2 = \text{floor}(y1/4)$

Network Design

The overall structure of the neural network was inspired by previous work applying deep learning to image segmentation22 and high-content screening23. The network of the present example has approximately $4.6 \times 10^5$ parameters arranged in six fully convolutional layers, 5 max pooling layers, one global mean layer, and one batch-normalization layer (FIG. 7). Through cross-validation on the training set, it was to use leaky rectifying linear neurons with cross-entropy loss. Importantly, it was that using a batch normalization layer24 was necessary for convergence. Over one batch of training data, a batch normalization layer produces outputs with zero mean and unit variance. In training, this leads to a well-distributed set of output predictions, which accelerates the learning process. In addition, a dropout layer was used, which randomly eliminates 50% of the neurons during each round of training to prevent co-adaptation of neurons (a form of over-fitting)25.

Using a global mean layer gives us the option of training the network on images of arbitrary size. However, training was performed on small patches extracted from sparse images to increase the relative size of the training set. Thus, during the training process, small patches (100×100 pixels, 200×200 μm) were randomly extracted from the downscaled feature maps (approx. 750×750 pixels, 1500×1500 μm) and assigned them the same class as the overall image. At runtime, these patches were randomly flipped and rotated (in multiples of 90 degrees) to augment the dataset and promote the learning of rotationally invariant features. Theoretically, the augmented training set consists of 108 different patches; however only a subset of these images was actually used to train the network.

Each layer in the neural network combines features from the previous layer, and deeper layers can learn higher order features. The model uses a fully convolutional architecture, which means that it can process images of arbitrary size, producing output in the form of a spatial map that scales with the size of the input image22. Thus, the final classification layer produces a spatial map for ER score over the image, and the average prediction over the map is treated as the score for the image.

All experiments were conducted on an Nvidia K80 GPU using the Deep Learning libraries Theano26 and Lasagne27.

Network Training 113 patients from the IDC dataset were randomly into training (n=57) and test (n=56) datasets. From the training set, 20% data was held out for cross validation during the training process. From the training set, small patches (100× 100 pixels, 200×200 μm) were subsampled and trained the network using image-level labels (ER+, ER−) for the patches and a cross-entropy loss function. After approximately 450 epochs (corresponding to training on approx. $7 \times 10^4$ individual patches), the training loss began to plateau (FIG. 9). The loss had plateaued by epoch 825, so the held-out cross-validation data was added back in and trained the net for approximately 1000 epochs to maximize accuracy on the entire training dataset.

Step 5: Testing the Neural Network

Following training, all parameters and weights in the neural network were fixed. Full sized images were classified and the predictions were stored in a text file for analysis. The test sets were held out during training and were only evaluated after the network had been trained.

Data Availability

The nuclear segmentations that were used to train the neural network are freely available under the Creative Commons CC-BY 4.0 license as MultiCellDS digital snapshots, included here as supplementary data21. In addition, the raw H&E images used to generate cell segmentations available from the website of Biomax.us (IDC, www.biomax.us/tissue-arrays/Breast/HBre-Duc140Sur-01), or the Dryad Digital Repository28 (DCIS Dataset).

While exemplary embodiments are described above, it is not intended that these embodiments describe all possible forms of the invention. Rather, the words used in the specification are words of description rather than limitation, and it is understood that various changes may be made without departing from d spirit and scope of the invention. Additionally, the features of various implementing embodiments may be combined to form further embodiments of the invention.

REFERENCES

1. Wang, D., Khosla, A., Gargeya, R., Irshad, H. & Beck, A. H. Deep Learning for Identifying Metastatic Breast Cancer. arXiv Prepr. 1-6 (2016).

2. Yu, K.-H. et al. Predicting non-small cell lung cancer prognosis by fully automated microscopic pathology image features. Nat. Commun. 7, 12474 (2016).
3. Allred, D. C. Issues and updates: evaluating estrogen receptor-α, progesterone receptor, and HER2 in breast cancer. Mod. Pathol. 23, S52-S59 (2010).
4. Gradishar, W. J. et al. NCCN Guidelines Version 1.2016 Breast Cancer Panel Members. Natl. Compr. Cancer Netw. (2016).
5. Goldstein, N. S., Hewitt, S. M., Taylor, C. R., Yaziji, H. & Hicks, D. G. Recommendations for improved standardization of immunohistochemistry. Appl Immunohistochem Mol Morphol 15, 124-133 (2007).
6. Elizabeth Hammond, M. H. et al. American Society of Clinical Oncology/College of American Pathologists Guideline Recommendations for Immunohistochemical Testing of Estrogen and Progesterone Receptors in Breast Cancer.
7. Ingle, J. N. et al. A Double-Blind Trial of Tamoxifen Plus Prednisolone Versus Tamoxifen Plus Placebo in Postmenopausal Women With Metastatic Breast Cancer.
8. Robert, N. Clinical Efficacy of Tamoxifen. Oncology (1997).
9. Wood, A. J. J. & Osborne, C. K. Tamoxifen in the Treatment of Breast Cancer. N. Engl. J. Med. 339, 1609-1618 (1998).
10. Krizhevsky, A., Sutskever, 1. & Hinton, G. E. ImageNet Classification with Deep Convolutional Neural Networks.
11. US Biomax, I. Breast carcinoma tissue microarray, 140 cases, with ER/PR/HER2 and survival data, followed up 9-12 years. (2015). Available at: http://www.biomax.us/tissue-arrays/Breast/HBre-Duc140Sur-01.
12. Dong, F. et al. Computational pathology to discriminate benign from malignant intraductal proliferations of the breast. PLoS One 9, 1-16 (2014).
13. Koboldt, D. C. et al. Comprehensive molecular portraits of human breast tumours. Nature 490, 61-70 (2012).
14. Janowczyk, A. & Madabhushi, A. Deep learning for digital pathology image analysis: A comprehensive tutorial with selected use cases. J. Pathol. Inform. 7, 29 (2016).
15. Williams, K. E. et al. Molecular phenotypes of DCIS predict overall and invasive recurrence. Ann. Oncol. Off. J. Eur. Soc. Med. Oncol. 26, 1019-25 (2015).
16. Zhou, W. et al. Molecular subtypes in ductal carcinoma in situ of the breast and their relation to prognosis: a population-based cohort study.
17. Comen, E., Norton, L.& Massagué, J. Clinical implications of cancer self-seeding. Nat. Publ. Gr. 8, 369-377 (2011).
18. Schindelin, J. et al. Fiji: an open-source platform for biological-image analysis. Nat. Methods 9, 676-682 (2012).
19. Schneider, C. a, Rasband, W. S. & Eliceiri, K. W. NIH Image to ImageJ: 25 years of image analysis. Nat. Methods 9.671-675 (2012).
20. Otsu, N. A Threshold Selection Method from Gray-Level Histograms. IEEE Trans. Syst. Man. Cybern. (1979).
21. Friedman, S. H. et al. MultiCellDS: a community-developed standard for curating microenvironment-dependent multicellular data. bioRxiv (2016).
22. Long J., Shelhamer, E.& Darrell, T. Fully Convolutional Networks for Semantic Segmentation.
23. Kraus, O. Z., Lei Ba, J. & Frey, B. J. Classifying and segmenting microscopy images with deep multiple instance learning. doi:10.1093/bioinformatics/btw252
24. Ioffe, S. & Szegedy, C. Batch Normalization: Accelerating Deep Network Training by Reducing Internal Covariate Shift. Arxiv 1-11 (2015). doi:10.1007/s13398-014-0173-7.2
25. Srivastava, N., Hinton, G., Krizhevsky, A., Sutskever, I. & Salakhutdinov, R. Dropout: A Simple Way to Prevent Neural Networks from Overfitting. J. Mach. Learn. Res. 15, 1929-1958 (2014).
26. Al-Rfou, R. et al. Theano: A Python framework for fast computation of mathematical expressions. (2016).
27. Dieleman, S. et al. Lasagne: First release. (2015). doi:10.5281/zenodo.27878
28. Dong, F. et al. Data from: Computational pathology to discriminate benign from malignant intraductal proliferations of the breast. PLOS ONE (2014). doi:doi:10.5061/dryad.pv85m

What is claimed is:

1. A method for determining a status of a diagnostic, prognostic, or theragnostic feature of a test stained tissue sample, comprising:
   (a) obtaining a sample digital image for the test stained tissue sample, the sample digital image comprising an associated set of spatial locations;
   (b) processing the sample digital image to generate a set of extracted features therefrom, wherein the set of extracted features comprises a morphometric feature of the test stained tissue sample;
   (c) associating a value for each extracted feature of the set of extracted features with each spatial location of the sample digital image to form a test set of extracted feature maps for the test stained tissue sample; and
   (d) processing the test set of extracted feature maps by a trained machine learning algorithm to determine the status of the diagnostic, prognostic, or theragnostic feature for the test stained tissue sample,
   wherein (d) further comprises a pre-processing operation comprising:
   (i) processing the test set of extracted feature maps by a first classifier to generate a first classification value, wherein the first classifier is trained on first training data comprising input nuclear morphometric features and associated diagnostic, prognostic, or theragnostic statuses,
   (ii) processing the test set of extracted feature maps by a second classifier to generate a second classification value, wherein the second classifier is trained on second training data comprising input cytoplasmic morphometric features and/or extracellular morphometric features and associated diagnostic, prognostic, or theragnostic statuses, and
   (iii) comparing the first classification value and the second classification value to determine which morphometric features are more predictive of the determined status.

2. The method of claim 1, wherein the set of extracted features comprises nuclear morphometric features, cytoplasmic morphometric features, extracellular morphometric features, colorimetric features, or a combination thereof.

3. The method of claim 2, wherein the nuclear morphometric features comprise nuclear size, nuclear shape, nuclear orientation, nuclear area, or nuclear perimeter, or a combination thereof.

4. The method of claim 2, wherein the colorimetric features comprise RGB pixels that describe colors within a structured biologic element.

5. The method of claim 1, wherein the set of extracted features comprises parameters for quantifying shapes of cellular and/or sub-cellular components.

6. The method of claim 5, wherein the set of extracted features comprises ellipse area, ellipse major axis length, ellipse minor angle length, or ellipse angle from horizontal, or a combination thereof.

7. The method of claim 5, wherein the cellular and/or sub-cellular components comprise individual cells, vacuoles, extra cellular space, or nucleolus, or a combination thereof.

8. The method of claim 1, wherein the set of extracted features comprises area, perimeter, circumference, fractal dimension, Zernike moments, or mitotic figure, or a combination thereof.

9. The method of claim 1, wherein the set of spatial locations comprises a 2-dimensional grid of spatial locations.

10. The method of claim 1, wherein the trained machine learning algorithm comprises a neural network, a Bayesian network, a decision tree algorithm, or a support vector machine, or a combination thereof.

11. The method of claim 10, wherein the neural network comprises a deep neural network, a convolutional neural network, or a deep convolutional neural network, or a combination thereof.

12. The method of claim 11, wherein the deep convolutional neural network comprises a plurality of convolutional layers, a plurality of pooling layers, a global mean layer, and a batch-normalization layer.

13. The method of claim 1, wherein the status of the diagnostic, prognostic, or theragnostic feature indicates presence or absence of a biomarker.

14. The method of claim 13, wherein the test stained tissue sample comprises a putative cancer sample.

15. The method of claim 14, wherein the putative cancer sample is a putative breast cancer sample.

16. The method of claim 15, wherein the biomarker comprises estrogen receptor (ER), progesterone receptor (PR), HER2, Ki67, a cytokeratin marker, or a combination thereof.

17. The method of claim 16, wherein the biomarker comprises ER.

18. The method of claim 15, wherein the putative breast cancer sample comprises an invasive ductal carcinoma (IDC) sample or a ductal carcinoma in situ (DCIS) sample.

19. The method of claim 15, wherein the biomarker comprises E-cadherin and PIK3CA, and wherein the status of the diagnostic, prognostic, or theragnostic feature indicates a subtype of breast cancer.

20. The method of claim 14, wherein the putative cancer sample is a putative lung cancer sample.

21. The method of claim 20, wherein the biomarker comprises EGFR, KRAS, c-Met, MET, or ALK, or a combination thereof.

22. The method of claim 13, wherein the biomarker comprises p53, Bcl-2, or c-Myc, or a combination thereof.

* * * * *